(12) United States Patent
Thörn et al.

(10) Patent No.: US 11,491,371 B2
(45) Date of Patent: Nov. 8, 2022

(54) DEVICE AND METHOD FOR MONITORING ACTIVITY PERFORMANCE

(71) Applicant: Sony Group Corporation, Tokyo (JP)

(72) Inventors: Ola Thörn, Limhamn (SE); Peter Exner, Malmö (SE)

(73) Assignee: Sony Group Corporation, Tokyo (JP)

( * ) Notice: Subject to any disclaimer, the term of this patent is extended or adjusted under 35 U.S.C. 154(b) by 392 days.

(21) Appl. No.: 16/830,636

(22) Filed: Mar. 26, 2020

(65) Prior Publication Data

US 2020/0338392 A1    Oct. 29, 2020

(30) Foreign Application Priority Data

Apr. 23, 2019 (SE) ..................... 1950494-3

(51) Int. Cl.
*A63B 24/00* (2006.01)
*G06T 7/73* (2017.01)
(Continued)

(52) U.S. Cl.
CPC ...... *A63B 24/0006* (2013.01); *A63B 24/0062* (2013.01); *B64C 39/024* (2013.01);
(Continued)

(58) Field of Classification Search
CPC ............ A63B 24/0006; A63B 24/0062; A63B 2024/0009; A63B 2024/0015;
(Continued)

(56) References Cited

U.S. PATENT DOCUMENTS 9,769,387 B1   9/2017  Beard et al.
2007/0026975 A1  2/2007  Marty et al.
(Continued)

FOREIGN PATENT DOCUMENTS

CN    108334099 A    7/2018
WO    03022369 A2    3/2003
(Continued)

OTHER PUBLICATIONS

Swedish Office Action and Search Report, SE Application No. 1950494-3, dated Oct. 31, 2019, 9 pp.
(Continued)

*Primary Examiner* — Masud Ahmed
(74) *Attorney, Agent, or Firm* — Myers Bigel, P.A.

(57) ABSTRACT

A control device operates a drone with an onboard camera. The control device obtains a current performance metric to be computed for an activity performed by an individual, determines, based on a positioning rule associated with the current performance metric, a selected relative position, SRP, between the individual and the onboard camera, identifies a reference plane of the individual, operates the drone to move the onboard camera from an initial relative position to attain the SRP in relation to the reference plane; operates the onboard camera, when in the SRP, to capture image(s) of the individual, and provides the image(s) for computation of the current performance metric for the activity performed by the individual. The SRP may be defined, by the positioning rule, to ensure that the orientation of the individual in the image(s) is relevant or optimal for the current performance metric.

18 Claims, 4 Drawing Sheets

(51) Int. Cl.
*B64C 39/02* (2006.01)
*G05D 1/00* (2006.01)
*G05D 1/12* (2006.01)

(52) U.S. Cl.
CPC .............. *G05D 1/0094* (2013.01); *G05D 1/12* (2013.01); *G06T 7/74* (2017.01); *A63B 2024/0009* (2013.01); *A63B 2024/0015* (2013.01); *A63B 2024/0068* (2013.01); *A63B 2220/05* (2013.01); *A63B 2220/806* (2013.01); *B64C 2201/127* (2013.01)

(58) Field of Classification Search
CPC ........ A63B 2024/0068; A63B 2220/05; A63B 2220/806; B64C 39/024; B64C 2201/127; G05D 1/0094; G05D 1/12; G06T 7/74; G16H 20/30
See application file for complete search history.

(56) References Cited

U.S. PATENT DOCUMENTS

| | | |
|---|---|---|
| 2015/0335949 A1 | 11/2015 | Lokshin et al. |
| 2016/0287937 A1 | 10/2016 | Fitzgerald et al. |
| 2017/0161561 A1* | 6/2017 | Marty ................ H04N 5/23293 |
| 2018/0046187 A1 | 2/2018 | Martirosyan et al. |
| 2019/0053762 A1* | 2/2019 | Saigh ..................... A61B 90/98 |
| 2019/0154871 A1* | 5/2019 | Leduc ................ G08B 13/1966 |
| 2019/0192053 A1* | 6/2019 | Saigh ................... A61B 5/1118 |

FOREIGN PATENT DOCUMENTS

| | | |
|---|---|---|
| WO | 2017/074499 A1 | 5/2017 |
| WO | 2019102498 A1 | 5/2019 |

OTHER PUBLICATIONS

Cao et al., "Realtime Multi-Person 2D Pose Estimation using Part Affinity Fields", 2017 IEEE Conference on Computer Vision and Pattern Recognition (CVPR), Honolulu, HI, USA, Jul. 21-26, 2017, 1302-1310.

Li et al., "Monocular Long-term Target Following on UAVs", 2016 IEEE Conference on Computer Vision and Pattern Recognition Workshops, Las Vegas, NV, Jun. 26-Jul. 1, 2016, pp. 29-37.

Shotton et al., "Efficient Human Pose Estimation from Single Depth Images", IEEE Transactions on Pattern Analysis and Machine Intelligence, vol. 35, No. 12, Dec. 2013, pp. 2821-2840.

Zhou, "Sparseness Meets Deepness: 3D Human Pose Estimation from Monocular Video", 2016 IEEE Conference on Computer Vision and Pattern Recognition (CVPR), Las Vegas, NC, Jun. 27-30, 2016, pp. 4966-4975.

"Communication with European Search Report", EP Application No. 20159554.3, dated Sep. 16, 2020, 11 pp.

* cited by examiner

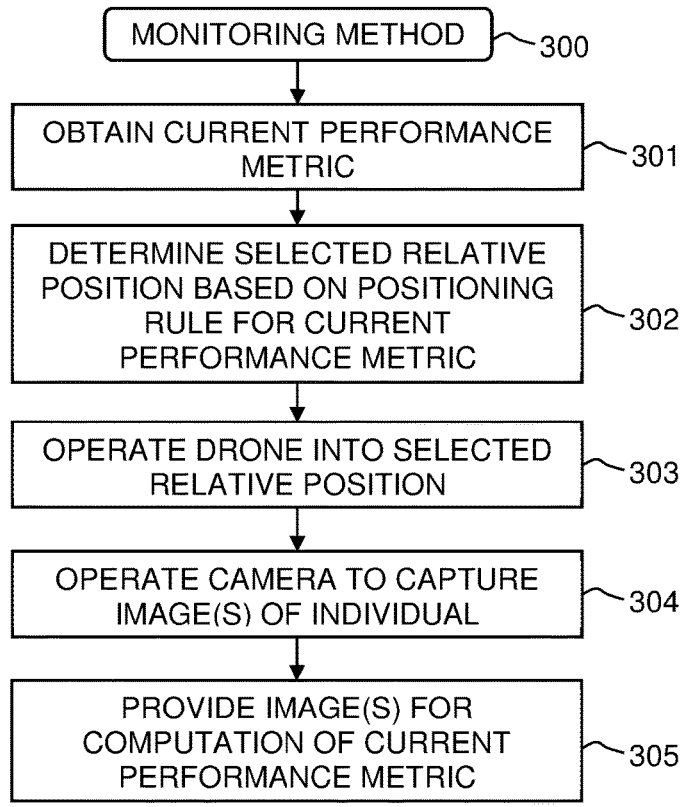
FIG. 3
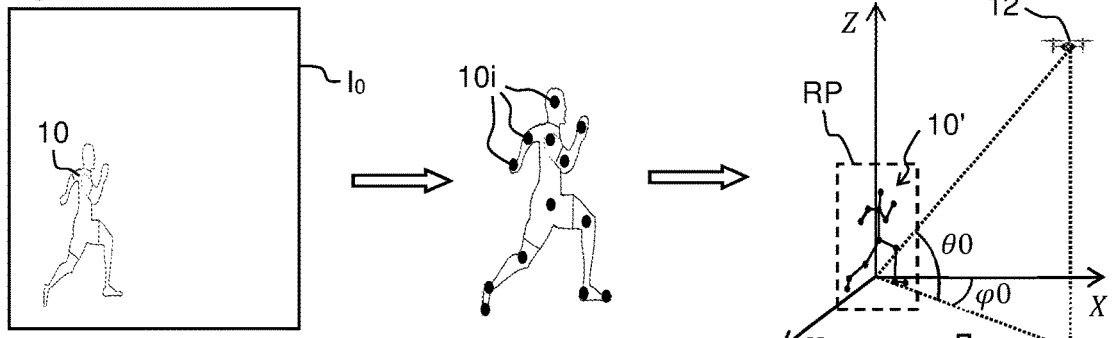
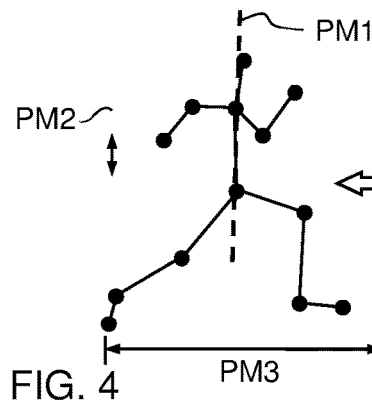
FIG. 4
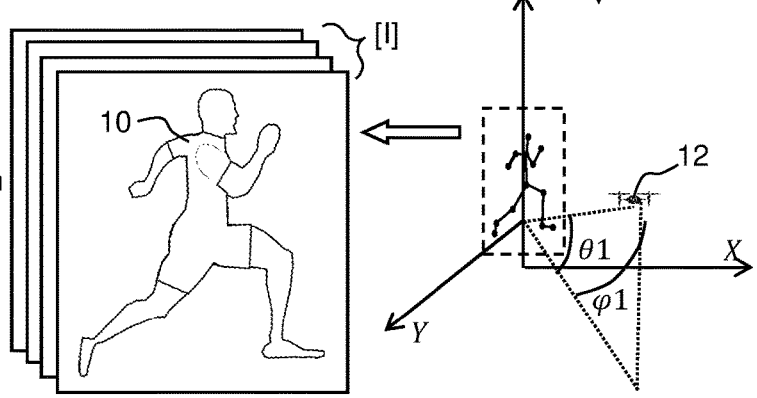

DEVICE AND METHOD FOR MONITORING ACTIVITY PERFORMANCE

RELATED APPLICATION

The present application claims the benefit of and priority to Swedish Patent Application No. 1950494-3, filed Apr. 23, 2019, the disclosure of which is incorporated herein by reference in its entirety.

TECHNICAL FIELD

The present invention relates generally to the field of activity equipment and, more particularly, to a technique for monitoring activity performance.

BACKGROUND

Both professional and amateur athletes are increasingly investing in technology to track their performance during training as well as competition. Monitoring systems are commercially available for measuring and recording performance metrics of athletic activities. Such monitoring systems include one or more sensors that are worn by the individual performing the athletic activity and may include a GPS, accelerometers, a pulse sensor, etc. The monitoring system may be generic and only capable of providing a few performance metrics, resulting in limited feedback to the wearer. There are also highly specialized systems for providing performance metrics that are targeted to a specific athletic activity, e.g. running.

While this type of wearable monitoring system may provide relevant feedback to the wearer, its reliance on wearable sensors restricts the available performance metrics. If further performance metrics are desired, the user must acquire another monitoring system and wear its sensors. Apart from the apparent risk for discomfort, the user many also be confronted with incoherent and unsystematic feedback from multiple systems.

It is also common to manually film an athlete during athletic activity to get both a comprehensive understanding of the athlete's performance and to identify room for improvement in the execution of the activity by detailed analysis of the footage.

Similar demands for performance monitoring may arise also for non-athletic activities such as rehabilitation training, physiotherapy, and medical evaluation, e.g. of foot alignment, gait, posture, etc.

It is known in the art to film individuals by use of unmanned aerial vehicles (UAVs), also known as drones. For example, U.S. Pat. No. 9,769,387 proposes an action camera system, which is located on an UAV and determines trackable objects and selects one as its target, either automatically or remotely according to user input. The trackable objects are distinct patterns worn by users, e.g. skiers. The action camera system is capable of automatically adjusting the position and speed of the UAV to maintain the orientation of the selected pattern in the recorded images, thereby causing the camera to follow a skier at a distance.

SUMMARY

It is an objective of the invention to at least partly overcome one or more limitations of the prior art.

A further objective is to provide a technique for activity monitoring that is flexible both with respect to the available performance metrics that may be provided and the types of activities that may be monitored.

A yet further objective is to provide an activity monitoring technique capable of yielding both detailed performance metrics and a comprehensive understanding of the performance.

One or more of these objectives, as well as further objectives that may appear from the description below, are at least partly achieved by a device, a system and a method for monitoring an athletic or physiological activity according to the independent claims, embodiments thereof being defined by the dependent claims.

Still other objectives, as well as features, aspects and technical effects of the present invention will appear from the following detailed description, the attached claims and the drawings.

BRIEF DESCRIPTION OF DRAWINGS

Embodiments of the invention will now be described in more detail with reference to the accompanying schematic drawings.

FIG. 3 is a flow chart of a monitoring method that may be implemented by the drone in FIG. 2.

FIG. 4 exemplifies data processing by the monitoring method in FIG. 3.

DETAILED DESCRIPTION OF EXAMPLE EMBODIMENTS

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure may satisfy applicable legal requirements. Like numbers refer to like elements throughout.

Also, it will be understood that, where possible, any of the advantages, features, functions, devices, and/or operational aspects of any of the embodiments of the present invention described and/or contemplated herein may be included in any of the other embodiments of the present invention described and/or contemplated herein, and/or vice versa. In addition, where possible, any terms expressed in the singular form herein are meant to also include the plural form and/or vice versa, unless explicitly stated otherwise. As used herein, "at least one" shall mean "one or more" and these phrases are intended to be interchangeable. Accordingly, the terms "a" and/or "an" shall mean "at least one" or "one or more", even though the phrase "one or more" or "at least one" is also used herein. As used herein, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention. As used herein, a "set" of items is intended to imply a provision of one or more items. The term "compute", and derivatives thereof, is used in its conventional meaning and may be seen to involve performing a calculation involving one or more mathematical operations to produce a result, e.g. by use of a computer.

It will furthermore be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing the scope of the present invention. As used herein, the term "and/or" includes any and all combinations of one or more of the associated listed items.

Figure 1:
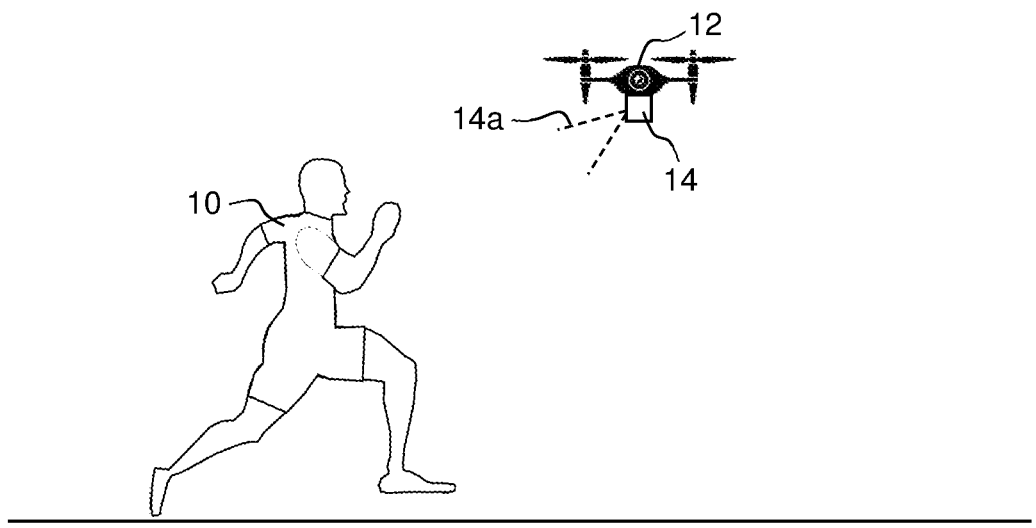
FIG. 1 shows a drone that films an individual performing an athletic activity.

Embodiments of the invention are related to quantitative monitoring of an activity performed by an individual 10, e.g. an athletic or non-athletic activity as exemplified in the Background section, by use of at least one drone 12 with at least one onboard camera 14, as shown in FIG. 1. Drones, also known as unmanned aerial vehicles (UAVs), are aircrafts controlled by an onboard automated control system, a ground-based control system or by a ground-based human pilot. The camera 14, which may be monocular or binocular, may be fixed or moveable in relation to the drone 12. For example, the onboard camera 14 may be attached to the drone 12 by one or more gimbals (not shown) that allow the camera 14 to rotate or move relative to the drone 12, as is known in the art. The quantitative monitoring involves computation of one or more quantitative performance metrics for the activity. In the example of FIG. 1, the individual 10 performs the activity of running, in training or competition. The performance of the running individual 10 may be quantified in terms of performance metrics such as cadence, stride length, vertical oscillation, horizontal oscillation, foot strike angle, posture, position of elbows, arm swing, speed, distance travelled, etc.

Embodiments of the invention involve automated control of the drone 12 not only to capture one or more images or frames of the individual 14 during the activity, but also to establish a predefined orientation of the field of view 14a of the camera 14 in relation to the individual 10, where the predefined orientation is specific to each performance metric to be quantified. As understood from the foregoing, the drone 12 may be controlled to attain the predefined orientation by moving the drone 12 in relation to the ground and/or by moving the camera 14 in relation to the drone 12.

Although the individual 10 in FIG. 1 is a human, embodiments of the invention are equally applicable to monitoring of an animal that performs an activity with or without human company, such as horse riding, dog racing, etc.

Figure 2:
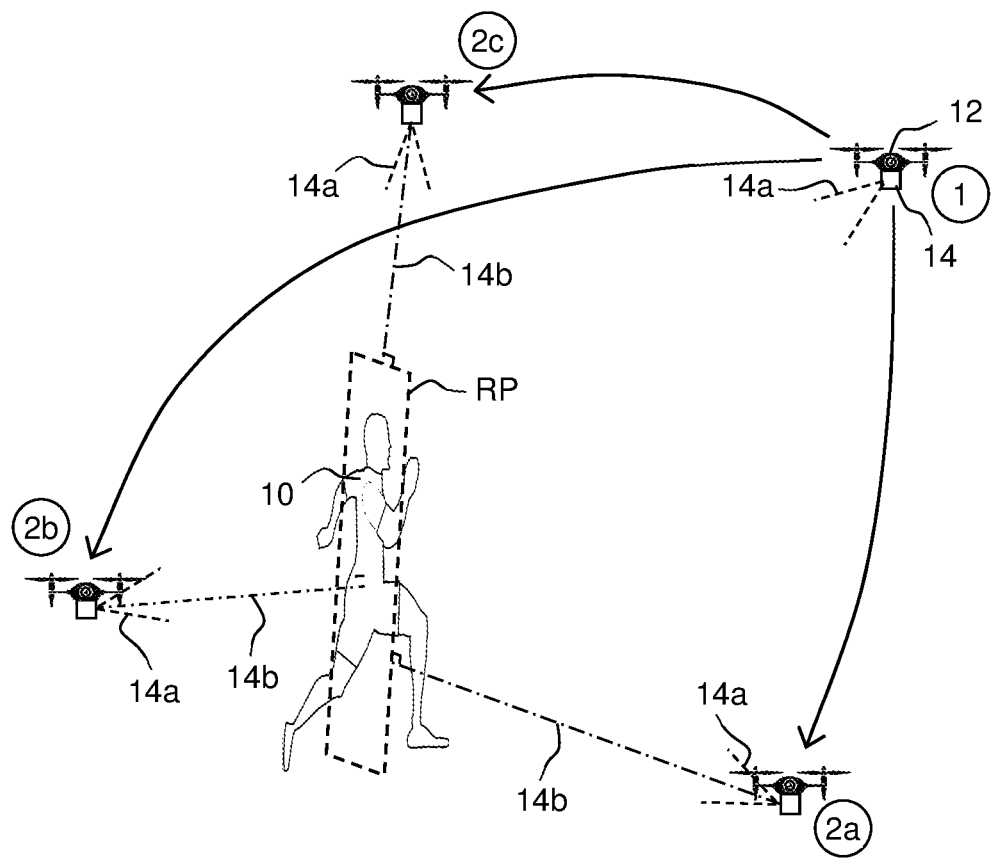
FIG. 2 illustrates movement of a drone from an initial position into relative positions associated with respective performance metrics.

Turning to FIG. 2, embodiments of the invention may involve determining a two-dimensional reference plane RP for the individual 10 and operating the drone 2 to establish and maintain the predefined orientation of the field of view (FOV) 14a in relation to the reference plane RP while operating the camera to capture one or more images. In the example of FIG. 2, the reference plane RP is effectively parallel to the extent of the torso of the individual 10. In a first example, the drone 12 may be moved from an initial position 1 into position 2a, in which the center line 14b of the FOV 14a extends in RP and is approximately perpendicular to the extent of RP in the height direction of the individual 10. The center line 14b may also be denoted "sightline" or "visual axis" of the camera 14. Among the above-mentioned examples of performance metrics, images taken in position 2a may be suitable for evaluation of, e.g., cadence, posture, stride length, foot strike angle or vertical oscillation. In a second example, the drone 12 may be moved from the initial position 1 into position 2b, in which the center line 14b is perpendicular to RP. Images taken in position 2b may be suitable for evaluation of, e.g., elbow position or horizontal oscillation. In a third example, the drone 12 may be moved from the initial position 1 into position 2c, in which the center line 14b extends in RP and is approximately perpendicular to the extent of RP in the width direction (i.e. the direction of shoulder width) of the individual 10. Images taken in position 2c may be suitable for evaluation of, e.g., cadence or elbow position. The positions 2a-2c are merely given as non-limiting examples. Other relative orientation(s) between RP and the center line 14b may be selected for image capture to evaluate any of the foregoing or other performance metrics.

FIG. 3 is a flow chart of a monitoring method 300 in accordance with an embodiment. The method 300 may be performed by a control device on the drone 12 or by a remote device which is operable to transmit control signals for the control device on the drone 12. Step 301 obtains a current performance metric (PM). The current PM may be obtained from a list of PMs to be evaluated for the activity performed by the individual 10, or may be input by an operator. The list of PMs may define a time-sequence of PMs to be evaluated for the individual 10. Step 302 determines a selected relative position (SRP) between the individual 10 and the camera 14 on the drone 12, by use of a positioning rule associated with the current PM. Step 303 operates the drone 12 into the SRP (cf. 2a-2c in FIG. 2), and step 304 operates the onboard camera 14 to capture one or more images of the individual 10 while performing the activity. Step 305 provides the image(s) for computation of the current PM. The method 300 may then return to step 301 to obtain and operate on a subsequent current PM. Depending on implementation, the image(s) may either be processed in real-time to provide the current PM or be stored for subsequent, off-line processing into the current PM. It is also conceivable, as described in detail below, to extract pose data from the image(s) and store the pose data for subsequent computation of the current PM.

By controlling the drone 12 to establish the SRP between the individual 10 and the onboard camera 14 for the respective PM, the method 300 ensures that the orientation of the individual 10 in the captured image(s) is relevant for the respective PM. Thus, by proper definition of the SRP, the accuracy of the PM may be high or even optimized. Further, the method 300 provides images and may thereby, in addition to quantitative PMs, help the individual 10 or another user gain a comprehensive understanding of the performance by manual or automated analysis and/or display of the images, or pose data extracted therefrom. The method 300 may also be simply extended to enable computation of additional PMs by providing, for use by the method, a respective additional positioning rule which is associated with and defines an SRP for the respective additional PM. Thereby, the method 300 offers full flexibility in terms of the PMs that may be computed and is also simply adaptable to monitoring of different types of activities.

The method 300 may be supplemented by conventional control algorithms for controlling the drone 12 to follow the movement of the individual 10, e.g. so that the drone 12 tracks the individual 10 while maintaining the SRP. Such tracking mechanisms are well-known in the art and are described, e.g., in aforesaid U.S. Pat. No. 9,769,387. Further, the control unit of the drone 12 may be equipped with a navigation system and built-in collision avoidance, which are also well-known in the art.

It may also be noted that the method 300 may define a relative movement of the drone 12 in relation to the individual 10 based on a sequence of different PMs to be evaluated, such that the drone 12 sequentially attains the SRPs of the PMs and captures one or more images in the respective SRP. For example, the method 300 may control the drone to follow the movement of the individual 10 while circling around the individual 10 essentially parallel to the ground, whereupon the images taken at SRPs associated with the sequence of PMs, such as positions 2a and 2b and positions diametral thereto in FIG. 2, may be processed for computation of the relevant PMs.

Further, step 304 need not be triggered by the drone 12 being in the SRP. In one embodiment, the method 300 may control the drone 300 to continuously film the individual 10 while moving around the individual 10 at different SRPs based on the PMs to be evaluated, whereupon step 305 selectively provides at least the images taken at the SRPs for computation of the PMs.

As noted in relation to FIG. 2, the positioning of the drone 12 (in step 303 of method 300) may involve determining a reference plane RP for the individual 10. In one embodiment, RP is determined as a function of sensor data from one or more sensors worn by the individual 10. For example, motion sensors may be placed at various locations on the body of the individual to measure the relative position, rotation, linear and/or angular acceleration and/or speed, etc. of those body locations. Based on such sensor data and GPS data from a GPS receiver on the body, the three-dimensional orientation of RP in a ground-based coordinate system may be computed in step 303 or obtained by step 303 from another process that computes the orientation of RP. Step 303 may then control the drone 12 to attain the SRP in relation to RP.

In another embodiment, step 303 computes the reference plane RP from images captured by the camera 14 on the drone 12. This embodiment has the advantage of being independent of additional sensors. Thus, the drone 12 may be autonomously controlled by the method 300 to attain any SRP. Such an embodiment will now be exemplified in further detail with reference to FIGS. 4-6.

Figure 5:
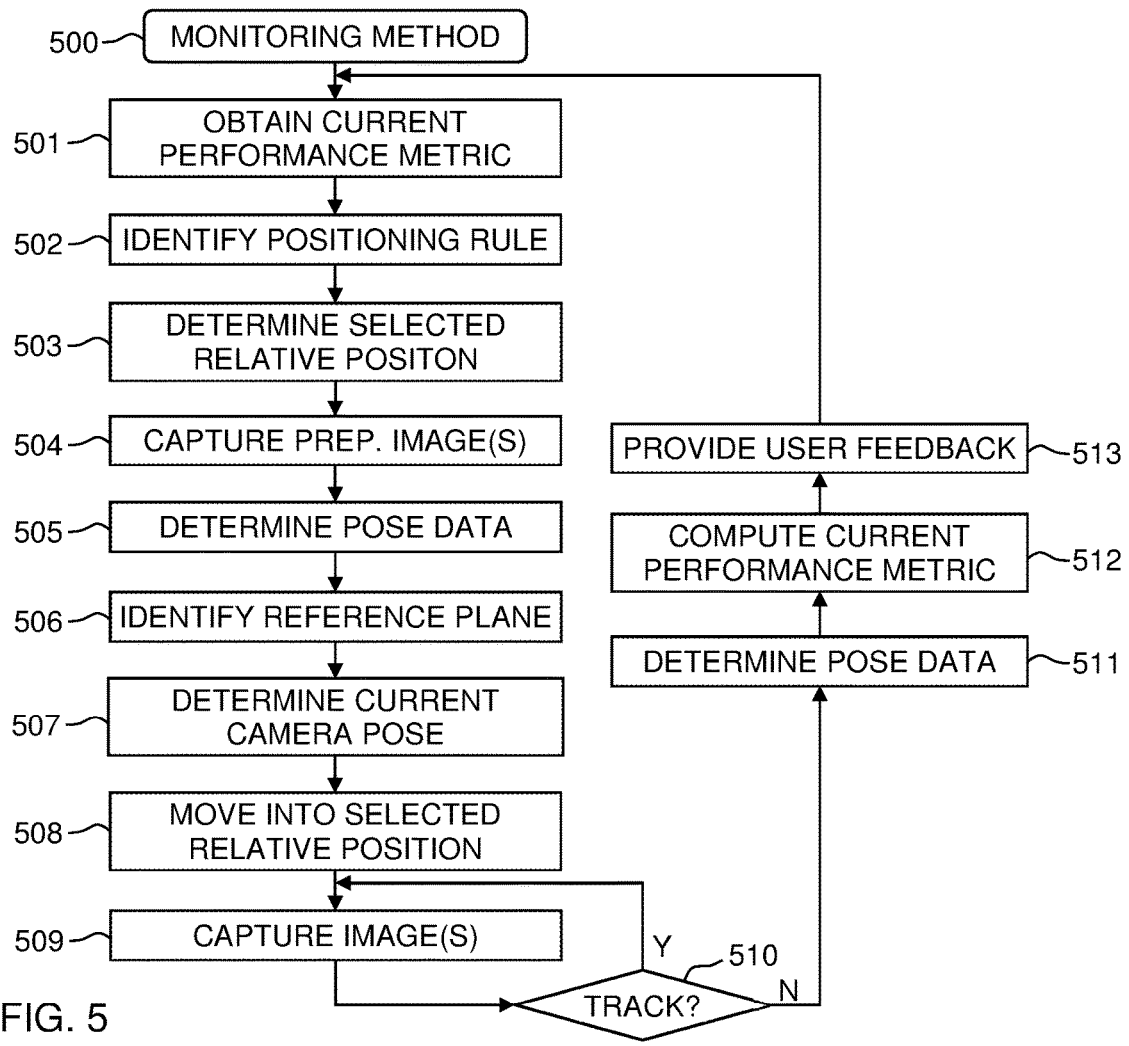
FIG. 5 is a flow chart of a detailed example of a monitoring method.

FIG. 5 is a flow chart of an example monitoring method 500. Step 501, which may correspond to step 301 in FIG. 3, obtains a current PM. Step 502 identifies a positioning rule for the current PM, e.g. by accessing a dedicated data structure (70a in FIG. 6). Step 503 determines the SRP from the positioning rule. Here, the SRP is defined in relation to a local coordinate system associated with the reference plane RP. The origin of the coordinate system may, but need not, have a predefined location in the RP. Step 504 captures one or more preparatory images $I_0$ of the individual 10, as exemplified in FIG. 4, at one or more locations of the camera 14. Step 505 then determines pose data for the individual 10 based on the preparatory image(s) $I_0$. As exemplified in FIG. 4, step 505 may process the image(s) $I_0$ for identification of a set of reference or key points 10i on the individual 10 representing its human pose. The reference points 10i may correspond to body features of the individual 10, such as body parts and/or joints between body parts. The pose data comprises the set of reference points 10i, optionally linked or connected in a skeleton representation 10' as shown to the right in FIG. 4. There are a multitude of available techniques for determining pose data in one or more images. Different techniques are described and referenced in "Efficient Human Pose Estimation from Single Depth Images" by Shotton et al, published in *IEEE Transactions on Pattern Analysis and Machine Intelligence*, Vol. 35, Issue. 12, 2013. Further techniques are described and referenced in "Realtime Multi-Person 2D Pose Estimation using Part Affinity Fields", by Cao et al, published in 2017 *IEEE Conference on Computer Vision and Pattern Recognition (CVPR)*, pp 1302-1310, 2017, as well as "Sparseness Meets Deepness: 3D Human Pose Estimation from Monocular Video", by Zhou et al, published in 2016 *IEEE Conference on Computer Vision and Pattern Recognition (CVPR)*, pp 4966-4975, 2016. Alternatively or additionally, the reference points 10i may correspond to or be determined as a function of a pattern of markers that are worn by the individual to be visible in the image(s) $I_0$. Such markers may, e.g., arranged at locations of particular relevance for the activity to be monitored.

Step 506 identifies the reference plane RP based on the reference points 10i and thereby identifies the orientation and location of the local coordinate system in 3D space. This is exemplified in FIG. 4, in which the RP is defined in relation to the skeleton representation 10', thereby also associating the local coordinate system (X,Y,Z) with the current pose of the individual 10.

Step 507 determines the current camera pose, and thus the current location of the drone 12, in relation to the local coordinate system (X,Y,Z). The current camera pose is inherently determined when the reference plane RP is determined in step 506. The camera pose may, e.g., be given by an azimuth angle $\varphi 0$ and an elevation angle $\theta 0$ in relation to the origin of the local coordinate system (X,Y,Z), and thus in relation to the reference plane RP. The camera pose may also include a current distance between the origin and the camera 14.

Step 508 then determines a movement trajectory from the current location of the drone to the SRP given by step 503 and controls the drone 12 for movement along the movement trajectory. It is understood that the movement trajectory may be updated during movement by the above-mentioned collision-avoidance mechanism on the drone 12. When the camera 14 is in the SRP, e.g., given by an azimuth angle $\varphi 1$ and an elevation angle $\theta 1$ in relation to the origin of the local coordinate system (X,Y,Z) as shown in FIG. 4, step 509 operates the camera 14 to capture a set of images, represented as [I] in FIG. 4.

The skilled person understands that it may be necessary to control the drone 12 to track the individual 10 between steps 504 and 509 to maintain the individual 10 within the field of view 14a (FIG. 2), e.g. by invoking a separate tracking mechanism. The tracking mechanism may be implemented in any known way, e.g., as described in aforesaid U.S. Pat. No. 9,769,387. Further, the method 500 may repeat steps 504-507 at one or more instances during the movement into the SRP to account for changes in RP. The method 500 thereby tracks the RP over time. Similarly, the method 500 may track the individual 10 and/or the RP during step 509, e.g. if a series of images are to be captured at the SRP within a time window. Such tracking is generally represented by step 510 in FIG. 5.

Step 511 determines pose data for the set of images [I] captured by step 509. The pose data may, e.g., comprise a set of reference points, optionally in a skeleton representation, for the respective image in the set of images [I].

Step 512 then processes the pose data for computation of the current PM. Depending on PM, pose data for a sequence of images captured by step 509 within a time window may be subjected to so-called kinematic analysis for computation of the PM. Kinematics is a branch of classical mechanics that describes the motion of points, objects, and groups of objects without considering the forces that caused the motion. The kinematic analysis of step 512 may involve determining gross movement of limb segments interconnected by joints, e.g. by describing relative 3D joint rotation by a Eulerian angle system, and/or performing detailed analysis of joint articulating surface motion, e.g. by describing generalized 3D, unconstrained rotation and translation by a screw displacement axis motion. However, kinematic analysis need not be used for determining the current PM.

FIG. 4 illustrates three examples of PMs that may be computed in step 511. In one example, a forward posture or lean PM1 may be determined from a single image and given as an angle relative to the direction of gravity. In another example, a vertical oscillation PM2 may be determined from a sequence of images and given as a distance or a percentage. In another example, a stride length PM3 may be determined from a sequence of images and given as a distance.

Figure 7A:
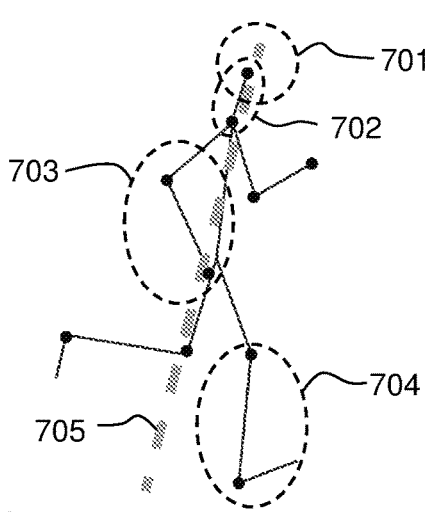
FIGS. 7A-7B exemplify computation of performance metrics.
Figure 7B:
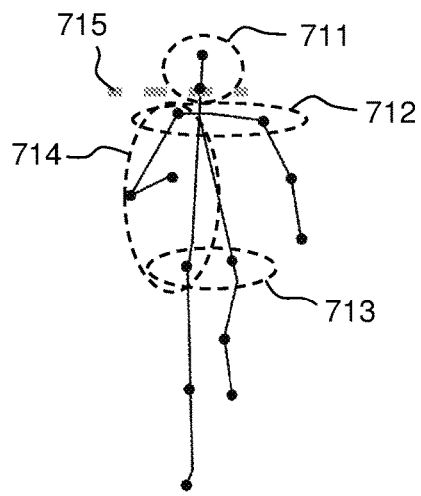

Further examples of step 511 are represented in FIGS. 7A-7B. FIG. 7A exemplifies regions that may be analyzed for computation of PMs in a side view of the individual (cf. position 2a in FIG. 2). Region 701 may yield head posture, e.g. direction of focus. Region 702 may yield vertical oscillation, i.e. a measure of the amount of movement up and down. Region 703 may yield elbow joint angle and arm swing. Region 704 may yield orientation of the lower leg, orientation of the foot between successive ground contacts, vertical oscillation of the foot, foot strike angle during the gait cycle, e.g. at initial contact, midstance and toe off (propulsion). Regions 703 and 704 may be jointly analyzed to yield the degree of synchronization between opposing arms and legs. In addition to local regions, the pose data may be processed for determination of global PMs, such as a measure of the whole-body posture which may be given by an inclination 705, as well as stride length, cadence, etc. FIG. 7B exemplifies regions that may be analyzed for computation of PMs in a front or rear view of the individual (cf. position 2b in FIG. 2). Region 711 may yield vertical oscillation and head posture. Region 712 may yield shoulder tension, orientation of the shoulders relative to ground, and vertical oscillation. Region 713 may yield hip balance. Region 714 may yield the degree of parallelism between arm and torso. In a further example, horizontal oscillation may be determined by analyzing movement of a reference line 715 representing the general transverse orientation of the upper body.

Figure 8:
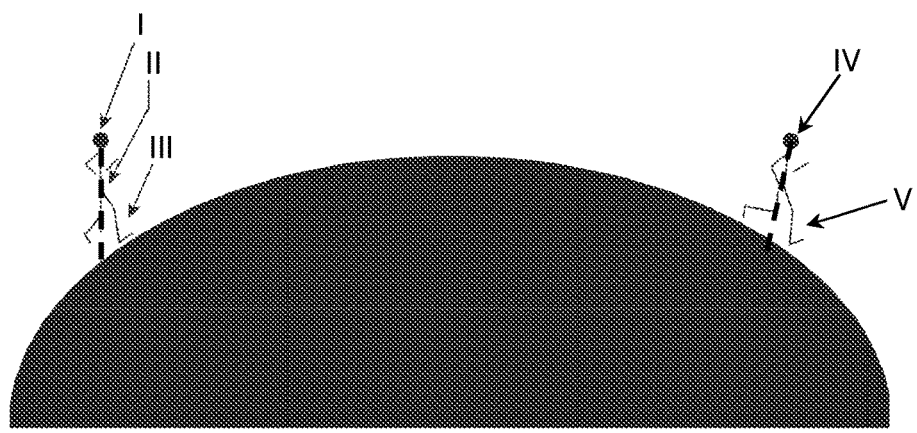
FIG. 8 exemplifies feedback provided to an individual performing an athletic activity.

Reverting to FIG. 5, the monitoring method 500 may include a step 513 that provides real-time feedback to the individual 10 or another person, e.g. on a display or through speakers. Such feedback may be quantitative and comprise one or more computed PMs. The feedback may also be qualitative and comprise advice on how to improve the performance. A non-limiting example of such feedback is schematically depicted in FIG. 8, which shows pose data for an individual running up and down a hill, given by images taken at right angles to the running direction. In the uphill scenario, the individual may be instructed to (I) adapt the head posture to look up the hill, (II) avoid leaning forward at the waist, and (III) take shorter strides and increase the knee lift. In the downhill scenario, the individual may be instructed to (IV) lean slightly forward, and (V) take shorter strides.

It is realized that step 513, steps 512-513 or steps 511-513 may be performed at a later time and separate from the method 500 if feedback need not be provided in real-time.

After step 513, the method 500 may return to step 501 to obtain a new current PM and repeat steps 502-513 for this PM. It may be noted that steps 504-505 may be omitted in this repetition of steps 502-513 and step 506 may instead operate on the pose data that was determined by step 511 in the preceding repetition. In a further variant, steps 504-506 are omitted and step 507 sets the current camera pose to the SRP that was determined by step 503 in the preceding repetition.

The foregoing description has presumed that only the individual 10 to be monitored is present in images captured by the onboard camera 14. However, the proposed methods 300, 500 may be extended to handle situations in which other individuals are also present in the images. For example, the tracking mechanism of the drone 12 may be set to track a specific individual in the images, and the methods 300, 500 may then select and operate on this specific individual in the images.

In situations when plural individuals perform the same activity, e.g. group training, mountaineering, power walking, steeplechasing, swimming, etc., the drone 12 may autonomously select the individual 10 to be monitored among a group of individuals. In one such embodiment, the method 500 may involve a preparatory process of operating the camera 14 to capture one or more preparatory images of the individuals in the group, processing the preparatory images to determine preparatory PMs for the individuals in the group, and selecting the individual 10 to be monitored based on the preparatory PMs. In one implementation, the preparatory process is performed before or as part of step 505 and may operate on the preparatory image(s) $I_0$ captured in step 504. However, to improve the accuracy of the preparatory PMs, the preparatory process may be performed in advance of the method 500 and include steps corresponding to steps 503-512 for each individual in the group, and a concluding step of selecting the individual to be monitored based on the preparatory PM for the respective individual. The method 500 may then be performed for the selected individual. The selected individual may, e.g., be the individual with the lowest or highest preparatory PM. If the preparatory process yields plural preparatory PMs for each individual, the selected individual may be chosen based on a "form index" generated by combining the preparatory PMs for the respective individual.

Figure 6:
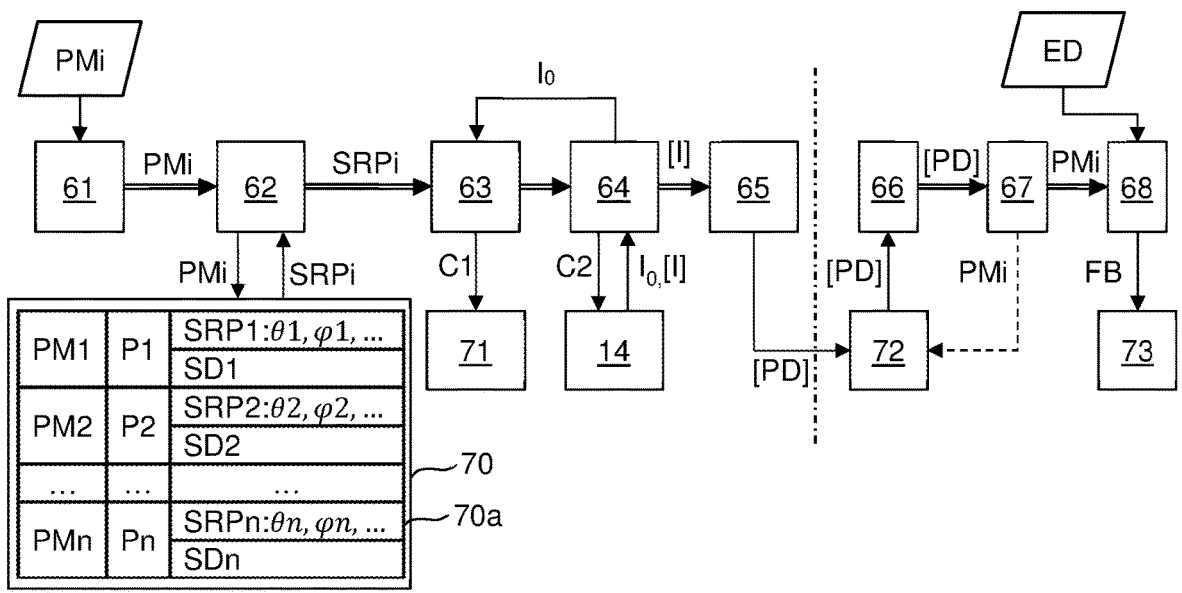
FIG. 6 is a block diagram of a processing pipeline for the monitoring method in FIG. 5.

FIG. 6 is a block diagram of an example system which is configured to implement the method 500 in FIG. 5. The system comprises blocks 61-68 that define a processing pipeline for monitoring activity performance. Block 61 implements step 501 and is configured to obtain the current performance metric, designated as PMi in FIG. 6. Block 62 implements steps 502-503 and is configured to determine a selected relative position, SRPi, for the PMi by accessing a data structure 70a stored in a memory 70. The data structure 70a is predefined and associates a respective performance metric PM1-PMn with a positioning rule P1-Pn. The respective positioning rule P1-Pn defines a selected relative position SRP1-SRPn, which may be given by the above-mentioned azimuth and elevation angles, and possibly one or more further position parameters such as distance. As indicated in FIG. 6, the respective positioning rule P1-Pn may further define secondary data SD1-SDn, which may define other control parameters of the drone 12 and/or the camera 14 such as (minimum) exposure time, (minimum) focal depth, zoom level, number of images to be captured, time between images, time window for image capture, etc. Thus, although not shown in FIG. 6, block 62 may also acquire secondary data SDi for PMi from the data structure 70a. Block 63 implements steps 505-508 and is configured to operate the drone 12 and the camera 14 into the SRPi determined by block 62, while optionally also taking SDi into account, by providing one or more control signals C1 to a motion controller 71 of the drone 12 and/or the camera 14. Block 64 implements steps 504 and 509 and is configured to provide one or more control signals C2 to the camera 14 so as to cause the camera 14 to capture the preparatory image(s) $I_0$ (cf. step 504) and the set of images [I] (cf. step 509), optionally in accordance with SDi. As indicated in FIG. 6, block 64 is further configured to provide the preparatory image(s) $I_0$ to block 63 for determination of the current camera pose (cf. steps 505-507). The set of images [I] is obtained by block 65 which implements step 511 and is configured to determine pose data [PD] for the individual in the set of images [I]. In the illustrated embodiment, blocks 61-65 are included in a control device on the drone 12, whereas blocks 66-68 are performed by a separate device. Therefore, block 65 is configured to provide the pose data [PD] for receipt and storage in a memory 72 in the separate device. Although not shown in FIG. 6, [PD] may be provided together with an indication of the corresponding PM to be computed (i.e. PMi). Further, block 65 may provide GPS data indicating the GPS position(s) of the drone 12 when the underlying set of images [I] was taken and/or the corresponding SRPi. Block 66 is configured to read pose data [PD] from memory 72 and provide the pose data [PD] to block 67, which implements step 512 and is configured to process the pose data [PD] for computation of PMi. Block 68 implements step 513 and is configured to provide quantitative and/or qualitative feedback FB on a feedback device 73, e.g., a display and/or a speaker. As indicated in FIG. 6, block 68 may obtain environment data ED that defines the terrain in the surroundings of the individual 10, e.g. based on the GPS data, possibly in combination with SRPi, and use the environment data ED when determining the feedback FB. The environment data ED may include elevation data (cf. slope in FIG. 8), surface condition, weather data, etc. In an off-line feedback scenario, as indicated by a dashed arrow, block 67 may store the PMi in the memory 72 for subsequent retrieval by block 68.

Figure 9:
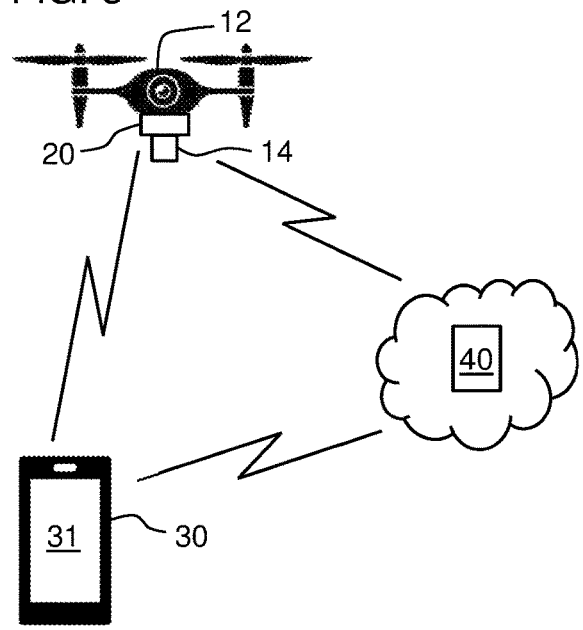
FIG. 9 exemplifies communication of data from a control device on a drone.

FIG. 9 illustrates an example system for activity monitoring in accordance with embodiments of the invention. The system includes a drone 12, a user device (UD) 30, and a server 40, e.g. a cloud server. The UD 30 may be any type of electronic device, such as a mobile phone, a PDA, a computer, a smart watch, a headset, etc. The drone 12 comprises one or more cameras 14 (one shown) and a control device (CD) 20, which is configured to perform at least part of the methods described herein. The drone 12 is further configured to communicate wirelessly with the UD 30 and/or the server 40. As shown, the UD 30 may be further configured to communicate, wirelessly or by wire with the server 40. The monitoring functionality as described herein may be partitioned between the drone 12, the UD 30 and the server 40 in different ways. In a first example, the drone 12 operates in accordance with a list of PMs to capture images [I]. The drone 12 transmits the images [I] to the server 40, which computes PMs and transmits corresponding FB to the UD 30 for presentation, e.g. on a display 31. In a second example, the drone 12 transmits the images [I] to the server 40, which computes and transmits [PD] to the UD 30, which computes PMs and presents corresponding FB. In a third example, which may correspond to the embodiment in FIG. 6, the drone 12 computes and transmits [PD] to the server 40, which computes PMs and transmits corresponding FB to the UD 30 for presentation. In a fourth example, which may also correspond to the embodiment in FIG. 6, the drone 12 computes and transmits [PD] to the UD 30, optionally via the server 40 for intermediate storage, whereupon the UD 30 computes PMs and presents corresponding FB. In a fifth example, the drone 12 transmits the images [I] to the UD 30, which computes PMs and presents corresponding FB. In a sixth example, all of the disclosed functionality is performed by the drone 12, which thus transmits the FB to the UD 30, optionally via the server 40.

Computing [PD] at the drone 12 has the advantage of reducing the required bandwidth of the system and preserving the privacy of the monitored individual, by reducing or obviating the need to transmit images within the system. On the other hand, it may be advantageous to compute [PD] and/or PMs at the UD 30 or the server 40 in order to reduce the required processing capability of the drone 12 and reduce its power consumption. Such a partitioning of functionality also makes it possible to compute the PMs and provide FB based on images and/or [PD] generated by two or more drones 12 that operate in synchronization in relation to the monitored individual 10 and in accordance with embodiments of the invention.

In a further variant of the system in FIG. 9, the images [I], the [PD] or the PMs are stored in a memory of the drone 12 and are transferred to either the UD 30 or the server 40, wirelessly or by wire, when the drone 12 has landed.

Figure 10:
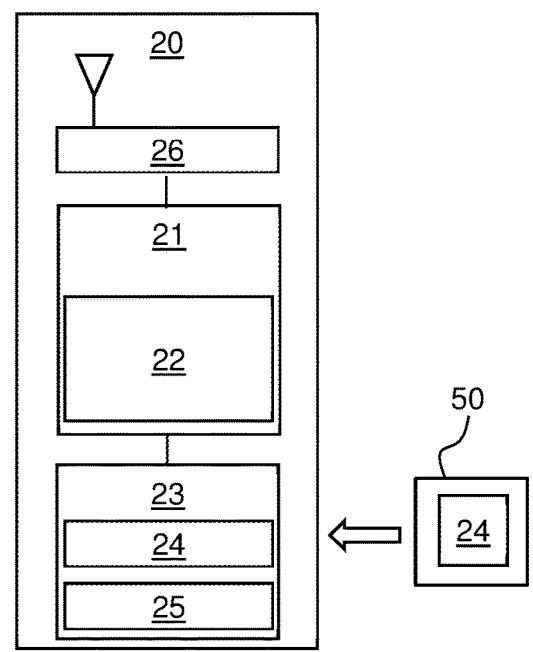
FIG. 10 is a block diagram of a control device in accordance with an embodiment.

FIG. 10 is a block diagram of an exemplifying structure of the CD 20 on the drone 12. Generally, the CD 20 may be configured to perform any of the methods described herein, or part thereof, by a combination of software and hardware circuitry, or exclusively by specific hardware circuitry. The CD 20 may, e.g., be or be part of the main flight controller on the drone 12. In FIG. 10, the CD 20 comprises a control circuit 21 responsible for the overall operation of the CD 20. As shown, the control circuit 21 may include a processing device or processor 22, which may be or include a central processing unit (CPU), graphics processing unit (GPU), microcontroller, microprocessor, ASIC, FPGA, or any other specific or general processing device. The processor 22 may execute instructions 23 stored in a separate memory, such as memory 23, and/or in an internal memory (not shown) of the control circuit 21, in order to control the operation of the CD 20. The instructions 24 when executed by the processor 22 may cause the CD 20 to perform any of the methods described herein, or part thereof. For example, the processing pipeline 61-65 in FIG. 6 may be implemented by the instructions 23. As indicated in FIG. 10, the memory 13 may also store data 25 for use by the processor 22, e.g., the data structure 70a (FIG. 6). The memory 23 may comprise one or more of a buffer, a flash memory, a hard drive, a removable media, a volatile memory, a non-volatile memory, a random access memory (RAM), or another suitable device. In an exemplary arrangement, the memory 23 includes a non-volatile memory for long term data storage and a volatile memory that functions as system memory for the control circuit 21. The memory 23 may exchange data with the control circuit 21 over a data bus. Accompanying control lines and an address bus between the memory 23 and the control circuit 21 also may be present. The memory 23 is considered a non-transitory computer readable medium. The CD 20 further includes a communication device 26 for wireless communication, e.g. with the UD 30 and/or the server 40 (FIG. 9). The communication device 26 may comprise at least one radio transceiver, at least one antenna, tuners, impedance matching circuits, and any other components needed for wireless communication. It may be noted that some functions of the described methods may be implemented in hardware, which may be invoked by the executing instructions 24 to produce a specific type of output from a specific type of input.

The instructions 24 may be supplied to the CD 20 on a computer-readable medium 50, which may be a tangible (non-transitory) product (e.g. magnetic medium, optical disk, read-only memory, flash memory, etc.) or a propagating signal.

Embodiments of the invention are applicable to any type of activity that may be monitored in terms of a performance metric computed from footage (film or still images) captured by a drone. Such activities include, without limitation, running, ball game playing, martial arts, skiing, ice skating, ski jumping, boxing, rowing, bicycling, swimming, track-and-field athletics, golf, workout, equestrian activity, mountaineering, rehabilitation training, power walking, and more.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

Further, while operations are depicted in the drawings in a particular order, this should not be understood as requiring that such operations be performed in the particular order shown or in sequential order, or that all illustrated operations be performed, to achieve desirable results. In certain circumstances, parallel processing may be advantageous.

In the following, a set of items are recited to summarize some aspects and embodiments of the invention as disclosed in the foregoing.

Item 1: A device for monitoring an activity, said device being configured to: obtain a current performance metric (PMi) to be computed for the activity; determine, based on a positioning rule associated with the current performance metric (PMi), a selected relative position (SRPi) between an individual (10) to be monitored and a camera (14) on a drone (12); operate the drone (12) to move the camera (14) from an initial relative position relative to the individual (10) into the selected relative position (SRPi); operate the camera (14), when in said selected relative position (SRPi), to capture one or more images ([I]) of the individual (10) performing the activity; and provide the one or more images ([I]) for computation of the current performance metric (PMi) for the activity performed by the individual (10).

Item 2: The device of item 1, which is further configured to: identify a reference plane (RP) of the individual (10) and operate the drone (12) to move the camera (14) to attain the selected relative position (SRPi) in relation to the reference plane (RP).

Item 3: The device of item 2, which is configured to at least partly define the selected relative position (SRPi) by an elevation angle ($\theta 1$) and an azimuth angle ($\varphi 1$) relative to an origin of a coordinate system associated with the reference plane (RP).

Item 4: The device of item 2 or 3, which is further configured to: determine a set of reference points (10$i$) of the individual (10) representing a current pose of the individual (10) and identify the reference plane (RP) as a function of the set of reference points (10$i$).

Item 5: The device of item 4, which is further configured to: operate the camera (14) to capture one or more preparatory images ($I_O$) of the individual (10), and process the one or more preparatory images ($I_O$) for determining the set of reference points (10$i$).

Item 6: The device of item 4 or 5, wherein at least a subset of the reference points (10$i$) represents body features of the individual (10).

Item 7: The device of any one of items 4-6, which is further configured to: determine, based on the set of reference points (10$i$), the initial relative position of the camera (14) in relation to the individual (10), determine a movement trajectory from the initial relative position to the selected relative position (SRPi), and operate the drone (12) in accordance with the movement trajectory.

Item 8: The device of any preceding item, wherein the positioning rule is defined to identify the selected relative position (SRPi) to ensure said computation of the current performance metric (PMi) based on the one or more images ([I]) of the individual (10) performing the activity.

Item 9: The device of any preceding item, which is further configured to: extract pose data ([PD]) from the one or more images ([I]) and provide the pose data ([PD]) for computation of the current performance metric (PMi).

Item 10: The device of any preceding item, which is further configured to: operate the camera (14) to capture one or more preparatory images ($I_O$) of a group of individuals, process the one or more preparatory images ($I_O$) to determine preparatory performance metrics of individuals in the group of individuals, and select the individual (10) to be monitored based on the preparatory performance metrics.

Item 11: A system comprising the device for monitoring an activity in accordance with any one of items 1-10, and the drone (12) with the camera (14).

Item 12: A method of monitoring an activity, said method comprising: obtaining (301; 501) a current performance metric (PMi) to be computed for the activity; determining (302; 503), based on a positioning rule associated with the current performance metric (PMi), a selected relative position (SRPi) between an individual (10) to be monitored and a camera (14) on a drone (12); operating (303; 508) the drone (12) to move the camera (14) from an initial relative position relative to the individual (10) into the selected relative position (SRPi); operating (304; 509) the camera (14), when in said selected relative position (SRPi), to capture one or more images ([I]) of the individual (10) performing the activity; and providing (305) the one or more images ([I]) for computation of the current performance metric (PMi) for the activity performed by the individual (10).

Item 13: The method of item 12, further comprising identifying (506) a reference plane (RP) of the individual (10), wherein the drone (12) is operated (303; 508) to move the camera (14) to attain the selected relative position (SRPi) in relation to the reference plane (RP).

Item 14: The method of item 13, wherein the selected relative position (SRPi) is at least partly defined by an elevation angle ($\theta 1$) and an azimuth angle ($\varphi 1$) relative to an origin of a coordinate system associated with the reference plane (RP).

Item 15: The method of item 13 or 14, further comprising: determining (505) a set of reference points (10$i$) of the individual (10) representing a current pose of the individual (10), wherein the reference plane (RP) is identified (506) as a function of the set of reference points (10$i$).

Item 16: The method of item 15, further comprising: operating (504) the camera (14) to capture one or more preparatory images ($I_0$) of the individual (10); and processing (505) the one or more preparatory images ($I_0$) for determining the set of reference points (10i).

Item 17: The method of item 15 or 16, wherein at least a subset of the reference points (10i) represents body features of the individual (10).

Item 18: The method of any one of items 15-17, further comprising: determining (507), based on the set of reference points (10i), the initial relative position of the camera (14) in relation to the individual (10); determining a movement trajectory from the initial relative position to the selected relative position (SRPi); and operating the drone (12) in accordance with the movement trajectory.

Item 19: The method of any one of items 12-18, further comprising: capturing, at one or more instances during movement from the initial relative position to the selected relative position (SRPi), one or more further preparatory images ($I_0$); identifying a current reference plane (RP) of the individual (10) in the one or more further preparatory images ($I_0$); and operating the drone (12) to attain the selected relative position (SRPi) in relation to the current reference plane (RP).

Item 20: The method of any one of items 12-19, wherein the positioning rule identifies the selected relative position (SRPi) to ensure said computation of the current performance metric (PMi) based on the one or more images ([I]) of the individual (10) performing the activity.

Item 21: The method of any one of items 12-20, further comprising: extracting (511) pose data ([PD]) from the one or more images ([I]); and providing the pose data ([PD]) for said computation of the current performance metric (PMi).

Item 22: The method of item 21, wherein the one or more images ([I]) comprises a time sequence of images, said method further comprising: computing the current performance metric (PMi) for the individual (10) by kinematic analysis of the pose data (PD) extracted from the time sequence of images.

Item 23: The method of any one of items 12-22, further comprising: operating the camera (14) to capture one or more preparatory images ($I_0$) of a group of individuals; processing the one or more preparatory images ($I_0$) to determine preparatory performance metrics (PMi) of individuals in the group of individuals; and selecting the individual (10) to be monitored based on the preparatory performance metrics (PMi).

Item 24: The method of any one of items 12-23, further comprising: computing (511, 512) the current performance metric (PMi) for the individual (10) based the one or more images ([I]).

Item 25: The method of item 24, further comprising generating (513), based on the current performance metric (PMi), feedback (FB) regarding the activity performed by the individual (10).

Item 26: The method of item 25, further comprising: obtaining environment data (ED) that defines one or more properties of the surroundings of the individual (10), wherein the feedback (FB) is generated as a function of the environment data (ED).

Item 27: The method of item 25 or 26, further comprising: presenting (512) said feedback (FB) to the individual (10).

Item 28: The method of any one of items 12-27, wherein the activity is included in the group of: running, ball game playing, martial arts, skiing, ice skating, ski jumping, boxing, rowing, bicycling, swimming, track-and-field athletics, golf, workout, equestrian activity, mountaineering, rehabilitation training, and power walking.

Item 29: The method of any one of items 12-28, wherein the current performance metric (PMi) is selected among a group comprising: cadence, stride length, vertical oscillation, horizontal oscillation, foot strike angle, posture, position of elbows, arm swing, speed, distance travelled, and shoulder orientation.

Item 30: A computer-readable medium comprising computer instructions (54) which, when executed by a processor (22), cause the processor (22) to perform the method of any one of items 12-29.

The invention claimed is:

1. A device for monitoring an activity, said device being configured to perform operations comprising:
    obtaining a current performance metric for the activity performed by an individual;
    determining, based on a positioning rule associated with the current performance metric for the activity performed by the individual, a selected relative position between the individual to be monitored and a camera on a drone;
    determining a set of reference points of the individual representing a current pose of the individual;
    identifying a reference plane of the individual as a function of the set of reference points;
    operating the drone to move the camera from an initial relative position relative to the individual to attain the selected relative position in relation to the reference plane;
    operating the camera, when in said selected relative position, to capture one or more images of the individual performing the activity; and
    providing the one or more images for computation of the current performance metric for the activity performed by the individual.

2. The device of claim 1, wherein the device is configured to at least partly define the selected relative position by an elevation angle and an azimuth angle relative to an origin of a coordinate system associated with the reference plane.

3. The device of claim 1, wherein the device is further configured to perform operations comprising:
    operating the camera to capture one or more preparatory images of the individual, and process the one or more preparatory images for determining the set of reference points.

4. The device of claim 1, wherein the device is further configured to perform operations comprising:
    determining at least a subset of the set of reference points to represent body features of the individual.

5. The device of claim 1, wherein the device is further configured to perform operations comprising:
    determining, based on the set of reference points, the initial relative position of the camera in relation to the individual,
    determining a movement trajectory from the initial relative position to the selected relative position, and
    operating the drone in accordance with the movement trajectory.

6. The device of claim 1, wherein the positioning rule is defined to identify the selected relative position to ensure determination of the current performance metric based on the one or more images of the individual performing the activity.

7. The device of claim 1, which is further configured to perform operations comprising:

extracting pose data from the one or more images and provide the pose data for computation of the current performance metric.

8. The device of claim 1, wherein the device is further configured to perform operations comprising:
operating the camera to capture one or more preparatory images of a group of individuals;
processing the one or more preparatory images to determine preparatory performance metrics of individuals in the group of individuals; and
selecting the individual to be monitored based on the preparatory performance metrics.

9. A system comprising the device for monitoring an activity in accordance with claim 1, and the drone with the camera.

10. A method of monitoring an activity, said method comprising:
obtaining a current performance metric for the activity performed by an individual;
determining, based on a positioning rule associated with the current performance metric for the activity performed by the individual, a selected relative position between an individual to be monitored and a camera on a drone;
determining a set of reference points of the individual representing a current pose of the individual;
identifying a reference plane of the individual as a function of the set of reference points;
operating the drone to move the camera from an initial relative position relative to the individual to attain the selected relative position in relation to the reference plane;
operating the camera, when in said selected relative position, to capture one or more images of the individual performing the activity; and
providing the one or more images for computation of the current performance metric for the activity performed by the individual.

11. The method of claim 10, further comprising:
determining, based on the set of reference points, the initial relative position of the camera in relation to the individual;
determining a movement trajectory from the initial relative position to the selected relative position; and
operating the drone in accordance with the movement trajectory.

12. The method of claim 10, further comprising:
capturing, at one or more instances during movement from the initial relative position to the selected relative position, one or more preparatory images;
identifying a current reference plane of the individual in the one or more preparatory images; and
operating the drone to attain the selected relative position in relation to the current reference plane.

13. The method of claim 10, further comprising:
extracting pose data from the one or more images; and
providing the pose data for said computation of the current performance metric.

14. The method of claim 13, wherein the one or more images comprises a time sequence of images, said method further comprising:
computing the current performance metric for the individual by kinematic analysis of the pose data extracted from the time sequence of images.

15. The method of claim 10, further comprising:
operating the camera to capture one or more preparatory images of a group of individuals;
processing the one or more preparatory images to determine preparatory performance metrics of individuals in the group of individuals; and
selecting the individual to be monitored based on the preparatory performance metrics.

16. The method of claim 10, further comprising:
computing the current performance metric for the individual based the one or more images.

17. The method of claim 16, further comprising:
generating, based on the current performance metric, feedback regarding the activity performed by the individual.

18. The method of claim 17, further comprising:
obtaining environment data that defines one or more properties of surroundings of the individual,
wherein the feedback is generated as a function of the environment data.

* * * * *